US010322309B2

(12) United States Patent
Feldman

(10) Patent No.: US 10,322,309 B2
(45) Date of Patent: Jun. 18, 2019

(54) WEIGHTED GARMENT

(71) Applicant: Doree Feldman, Princeton, NJ (US)

(72) Inventor: Doree Feldman, Princeton, NJ (US)

(73) Assignee: Doree Feldman, Princeton, NJ (US)

( * ) Notice: Subject to any disclaimer, the term of this patent is extended or adjusted under 35 U.S.C. 154(b) by 74 days.

(21) Appl. No.: 15/706,023

(22) Filed: Sep. 15, 2017

(65) Prior Publication Data

US 2018/0085620 A1    Mar. 29, 2018

Related U.S. Application Data

(63) Continuation-in-part of application No. 14/854,026, filed on Sep. 14, 2015, now Pat. No. 9,795,821.
(Continued)

(51) Int. Cl.
| | |
|---|---|
| *A41B 1/08* | (2006.01) |
| *A41C 1/00* | (2006.01) |
| *A41C 3/00* | (2006.01) |
| *A41C 3/02* | (2006.01) |
| *A41D 1/04* | (2006.01) |

(Continued)

(52) U.S. Cl.
CPC ............ *A63B 21/065* (2013.01); *A41C 3/005* (2013.01); *A41C 3/0057* (2013.01); *A41D 1/04* (2013.01); *A61F 5/02* (2013.01); *A63B 21/4007* (2015.10); *A63B 23/0238* (2013.01); *A41B 1/08* (2013.01); *A41C 1/00* (2013.01); *A41C 3/02* (2013.01);
(Continued)

(58) Field of Classification Search
CPC .............. A63B 21/065; A63B 21/4007; A63B 21/4005; A63B 21/4025
See application file for complete search history.

(56) References Cited

U.S. PATENT DOCUMENTS 4,262,832 A  *  4/1981  Perkins .................... A41D 1/04
                                                    2/102
4,621,808 A     11/1986  Orchard et al.
(Continued)

FOREIGN PATENT DOCUMENTS

| EP | 0163305 B1 | 7/1991 |
| RU | 29473 U1 | 5/2003 |

OTHER PUBLICATIONS

"U.S. Appl. No. 14/854,026, Corrected Notice of Allowance dated Aug. 11, 2017", 5 pgs.
(Continued)

*Primary Examiner* — Garrett K Atkinson
(74) *Attorney, Agent, or Firm* — Schwegman Lundberg & Woessner, P.A.

(57) ABSTRACT

A garment to provide targeted training of small muscles along a spine of a user. The garment can be configured to extend around a torso of a user from an upper end portion to a lower end portion. A plurality of weights can be distributed and arranged along the body. The body and the plurality of weights can be configured to conform to the fleshy part of a user's body and to provide deep touch pressure compression of the plurality of weights to the torso to target the small postural muscles supporting the spine of a user when worn by the user, to engage and train the small postural muscles of the spine. The plurality of weights can be movable relative to one another with movement of the vertebrae of the user's spine, and the weights can be configured to move in a corresponding motion with the vertebrae of the user.

20 Claims, 9 Drawing Sheets

Related U.S. Application Data

(60) Provisional application No. 62/052,998, filed on Sep. 19, 2014.

(51) Int. Cl.
  *A61F 5/02* (2006.01)
  *A63B 21/00* (2006.01)
  *A63B 23/02* (2006.01)
  *A63B 21/065* (2006.01)

(52) U.S. Cl.
  CPC ...... *A41D 2400/32* (2013.01); *A41D 2600/10* (2013.01)

(56) References Cited

U.S. PATENT DOCUMENTS

| | | | |
|---|---|---|---|
| 4,658,442 A * | 4/1987 | Tomlinson | A63B 21/065 2/102 |
| 5,067,484 A | 11/1991 | Hiemstra-paez | |
| 5,120,288 A | 6/1992 | Sinaki | |
| 5,144,694 A * | 9/1992 | Conrad Da oud | A63B 21/065 2/102 |
| 5,211,163 A | 5/1993 | Mortenson | |
| 5,951,446 A * | 9/1999 | Monforte | A63B 21/065 2/456 |
| 6,005,041 A | 12/1999 | Cook | |
| 7,022,095 B2 | 4/2006 | Schneider | |
| 7,090,558 B2 | 8/2006 | Ott | |
| 7,708,673 B2 | 5/2010 | Gibson-horn | |
| 8,215,773 B2 | 7/2012 | Gibson-horn et al. | |
| 8,443,465 B2 * | 5/2013 | Stewart | A63B 21/0601 2/102 |
| RE46,069 E | 7/2016 | Gibsonhorn et al. | |
| 2002/0010058 A1 * | 1/2002 | Myrick | A63B 21/065 482/92 |
| 2004/0259666 A1 | 12/2004 | Bjugstad et al. | |
| 2010/0248915 A1 | 9/2010 | Gibson-horn | |
| 2016/0082302 A1 | 3/2016 | Feldman | |

OTHER PUBLICATIONS

"U.S. Appl. No. 14/854,026, Examiner Interview Summary dated May 30, 2017", 3 pgs.

"U.S. Appl. No. 14/854,026, Final Office Action dated Mar. 24, 2017", 10 pgs.

"U.S. Appl. No. 14/854,026, Non Final Office Action dated Aug. 16, 2016", 8 pgs.

"U.S. Appl. No. 14/854,026, Notice of Allowance dated Jun. 16, 2017", 9 pgs.

"U.S. Appl. No. 14/854,026, Preliminary Amendment filed Sep. 16, 2015", 30 pgs.

"U.S. Appl. No. 14/854,026, Response filed May 23, 2017 to Final Office Action dated Mar. 24, 2017", 10 pgs.

"U.S. Appl. No. 14/854,026, Response filed Nov. 10, 2016 to Non Final Office Action dated Aug. 16, 2016", 11 pgs.

"Entrain", [Online] Retrieved from the Internet : <http://www.dictionary.com/browse/entrain?s=t>.

Evans, B, et al., "An exploration of the effects of weighted garments on balance and gait of stroke patients with residual disability", short; Sage Jornal; Clin Rehabil vol. 15 No. 4390397, [Online] Retrieved from the Internet : <http://cre.sagepub.com/Content/15/4/390>, (Apr. 2001).

Kaminsky, "W8FIT Weighted Activewear Apparel Launch—Yoga-Run-Dance", Kickstarter.com, [Online] Retrieved from the Internet: <http://web.archive.org/web/20120429053558> <http://www.kickstarter.com/projects/w8fitlw8fit-weighted-activewear-launch-yoga-run-dance?>, (Nov. 2016), 7 pgs.

Salem, G J, et al., "A randomized trial of weighted west use in ambulatory older adults: strength, performance, and quality of life outcomes", Journal of the American Geriatrics Society, [Online] Retrieved from the Internet : <http://www.ncbl.nlm.nih.gov/pubmed/10733058>, (Mar. 2000).

\* cited by examiner

WEIGHTED GARMENT

This application is a continuation-in-part application and claims the benefit of U.S. patent application Ser. No. 14/854,026 by the same inventor, filed on Sep. 14, 2015 and hereby incorporates that application herein in its entirety. This application also claims the benefit of U.S. Provisional Patent Application No. 62/052,998 by the same inventor, filed on Sep. 19, 2014 and hereby incorporates that application herein in its entirety.

FIELD

This disclosure relates to a garment or a portion of a garment having weights.

Figure 2:
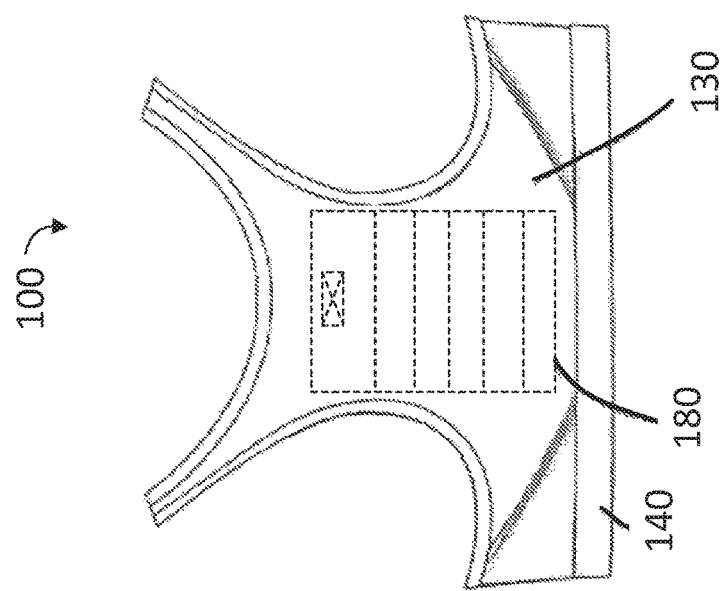
FIG. 2 depicts a back view of the garment in FIG. 1.

In the following description, like reference numbers are used to identify like elements. Furthermore, the drawings are intended to illustrate major features of exemplary examples in a diagrammatic manner. The drawings are not intended to depict every feature of every implementation nor relative dimensions of the depicted elements, and are not drawn to scale.

DETAILED DESCRIPTION

Described herein are weighted garments for improving posture. While there are numerous weighted garments used for exercising, many of the weighted garments have features limiting their use. Weighted garments for enhancing the effect of exercise, such as weighted vests, can hit hard against the body while the user is running and can be bulky and limit flexibility of the user. These and other characteristics can limit the time and occasion of use of these devices. Also, these devices are not generally designed to be unobtrusively worn under street clothes to provide increased exertion during normal daily activities. There is a need for weighted garment technology that can be comfortable to wear for long periods of time and that can be worn, undetected, under street clothes. The disclosure herein describes weighted garment technology that is configured to engage smaller postural muscles that support good posture. These muscles can include back muscles that support posture, but also other muscles circumferentially located around the spine.

In view of the above limitations, there is a need for a weighted garment that is comfortable to wear for extended periods of time while walking, running, bending, stretching, sitting, and so on.

Some benefits of the garments disclosed include helping people with spinal disorders. People with certain spinal disorders (e.g., degenerative disc disease, collapsed discs) should not necessarily move or exercise repetitively in some of directions. For example, some people should not do repetitive flexing exercises such as sit-ups or rotational exercises. However, it is important that these people strengthen these very same muscles. This presents an interesting quandary.

The inventor has discovered that placing weights over these muscles with deep pressure compression increases the workload that these muscles must overcome to function in the course of their normal daily activities, without repetitive gym type exercises. The garments described herein can include locating weights circumferentially around the core muscles using deep pressure compression to allow the postural muscles, including deeper and smaller muscles to be weight loaded in all planes of motion that will occur during activity.

The garments described herein combine light weights moved over a longer period of time as opposed to a heavier weight for a briefer period of time. The combination of the lighter weight that is located as shown in some examples with deep pressure compression allows the person wearing the garment to target these core postural muscles and to strengthen throught the course of their normal daily movement.

Many traditional exercises tend to work the body in the coronal and sagittal planes. Exercises that emphasize the transverse plane of motion tend to incorporate a rotational element to them. Doctors often advise against repetitive rotation movement as it can be injurious to the spine.

In the following description, numerous specific details are set forth to clearly describe various specific examples disclosed herein. One skilled in the art, however, will understand that the presently claimed invention may be practiced without all of the specific details discussed below. In other instances, well known features have not been described so as not to obscure the disclosure.

Various example garments are disclosed herein. Features disclosed in relation to one example, such as the garment 100 of FIG. 1, can be included in other garments, such as example garment 400 of FIGS. 14A and 14B.

Figure 1:
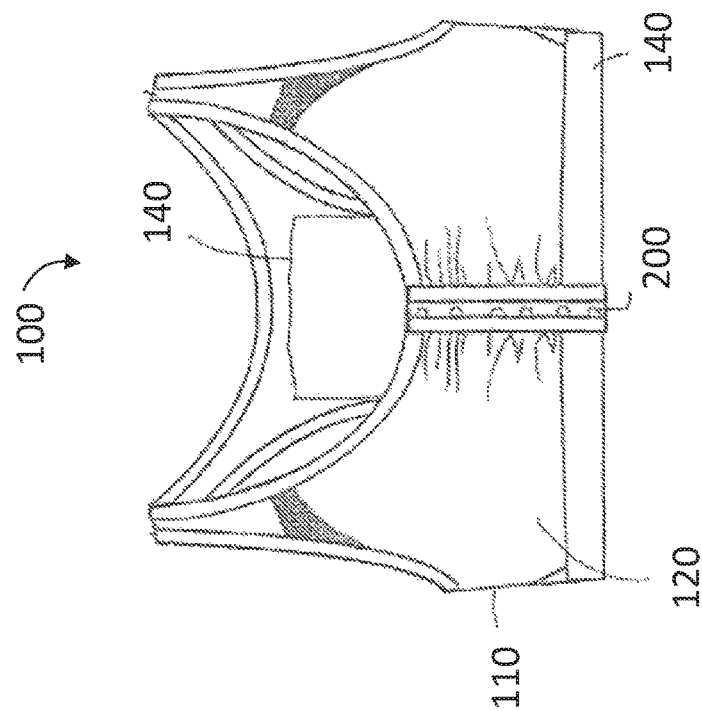
FIG. 1 depicts a front view of a garment, in accordance with at least one example.
Figure 3:
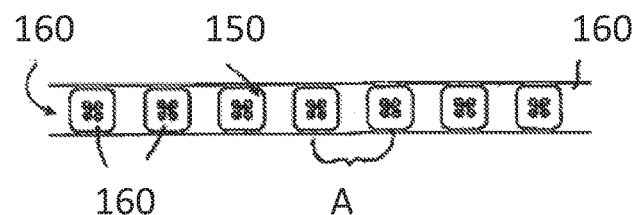
FIGS. 3-4 depict an elastic portion, in accordance with at least one example.
Figure 4:
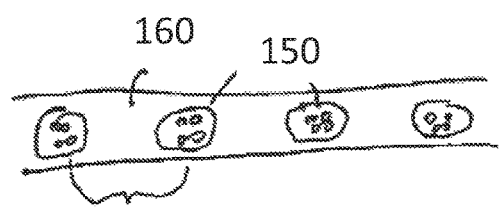

An illustrative example of a weighted garment 100 is shown in FIGS. 1-2. The garment 100 can include a body 110 having a front section 120 and a back section 130. In some examples, the garment 100 can include an elastic portion 140. In some examples, the elastic portion 140 can include a plurality of weights 150 coupled with an elastic material 160 as shown in FIG. 3. The plurality of weights 150 can be separated by a distance A (shown in FIG. 3) when the garment 100 is not being worn by a user. The plurality of weights 150 can be separated by a distance B (shown in FIG. 4) when the garment 100 is being worn by the user. Because the elastic material 140 stretches when the garment 100 is being worn by a user, the distance B is greater than the distance A. By being directly attached to an elastic portion of a garment, the weights can be held close to the wearer's body without necessarily requiring an outer layer of fabric.

Figure 5:
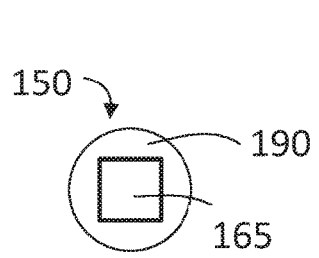
FIG. 5 depicts an insert, in accordance with at least one example.

In some examples, the weights 150 comprise metal, polymer, silicone, rubber and/or combination of these and/or other suitable materials. In some examples, at least one weight 150 can include metal 165 incased in soft material 170 as shown in FIG. 5. In some embodiment, the soft material 170 is silicone, rubber, foam and/or combination of these and/or other suitable materials. In some examples, at least one weight 150 is sewn to, glued to, and/or Velcro with the elastic material 160. In some examples, the elastic material 160 can include Nylon material, Spandex material, Jersey material, Polyester material, Cotton material and/or combination of any of these materials. In some examples, at least two of the weights 150 have different weights. In some examples, the plurality of weights 150 and the elastic material 160 are removably coupled with the elastic portion 140. In some examples, the plurality of weights 150 and the elastic material 160 are replaceable with another set of weights coupled with elastic material (not shown).

In some examples the weights are fixed to the elastic material. In that case, there may be no need for inserts or pockets.

In some examples, the garment 100 can include at least one compartment 180 coupled with the back section 130. In some embodiment, the compartment 180 is coupled with an inner surface of the back section 130, wherein the inner surface of the back section 130 is the closest to the user's skin. In some embodiment, the compartment 180 is coupled with an outer surface of the back section 130, wherein the outer surface of the back section 130 is the farthest from the user's skin. In some examples, the compartment 180 is sewn to, glued to, and/or Velcroed with the back section 130. In some examples, the compartment 180 is removably coupled with the back section 130.

In some examples the weights comprise a gel that has small pieces of a heavy substance embedded in it. This can make a weight that is flexible and sewable and that protects the body due to its softness and flexibility.

Figure 6:
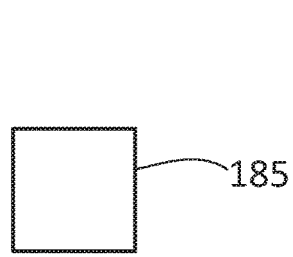
FIG. 6 depicts another insert, in accordance with at least one example.
Figure 7:
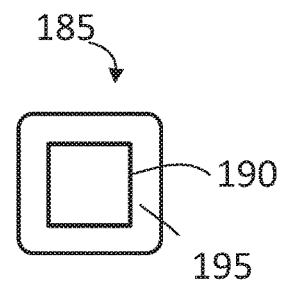
FIG. 7 depicts another insert, in accordance with at least one example.

In some examples, the compartment 180 can be configured to accommodate at least one insert 185 as shown in FIG. 6. In some examples, the insert 185 can include metal, polymer, silicone, rubber and/or combination of these and/or other suitable materials. In some examples, the insert 185 can include metal 190 incased in soft material 195 as shown in FIG. 7. In some embodiment, the soft material 195 can be silicone, rubber, foam and/or combination of these and/or other suitable materials.

In some examples, the insert 185 can be removably coupled with the compartment 180. In some examples, the insert 185 can be sewn to, glued to, and/or Velcro with the compartment 180. In some examples, additional inserts (not shown) are coupled with the compartment 180.

In some examples, the insert 185 can be replaceable with another insert (not shown). In some examples, additional inserts (not shown) are coupled with the insert 185.

In some examples, the insert 185 can be removably coupled with the garment 100. In some embodiment, the insert 185 can be coupled with an inner surface of the garment 100, wherein the inner surface of the garment 100 can be the closest to the user's skin. In some examples, the insert 185 can be coupled with an outer surface of the garment 100, wherein the outer surface of the garment 100 can be the farthest from the user's skin. In some examples, the insert 185 can be sewn to, glued to, and/or attached with hook and loop fastener to the garment 100. In some examples, the insert 185 can be removably coupled with the garment 100. In some examples, additional inserts (not shown) are coupled with the garment 100. In some examples, additional inserts (not shown) are coupled between the insert 185 and the garment 100.

In some examples, the insert 185 can be configured to provide padding and protection to the user's spine. The insert 185 allows for comfort in sitting and supine positions.

In some examples, the garment 100 can include one or more coupling members 200 to allow the user to put-on and remove the garment 100. In some examples, the one or more coupling members 200 are clasps, hooks, buttons and/or any other appropriate fasteners.

Although the garment 100 can be shown as a brassiere, it is to be understood that it can also be a vest, a t-shirt, a shirt, waist trainer, waist band, corset, back brace or any other clothing configured to be worn by a human being.

In some examples, the garment 100 can include a high-lycra content fabric. In some examples, the back section 130 of the garment 100 can include an inner layer, a middle layer(s) and an outer layer (not shown). The inner layer can be in physical contact with the user's skin and can include material washable, flexible, nonirritating material. In some examples, the middle layer can include multiple layers. In some examples, the middle layer, disposed between the inner layer and the outer layer, can be configured to support the insert 185. In some examples, the middle layer can include elastic material (with recoil properties) configured to support the insert 185 firmly in position against the user's body. In some examples the one or more middle layers are coupled with the bottom of the bottom band or other areas of that band to provide increased support to the compartment 180 and/or insert 185. In some examples the outer layer can be secured in a like manner. In some examples, the outer layer can include elastic material configured to hold the insert 185 firmly against the user's body preventing movement of the insert 185 during activity. The materials can include moisture wicking or odor control types of material.

In some examples, the garment 100 and other example garments disclosed herein (e.g., garment 400, FIGS. 14A and 14B) can be designed to be worn by a man or woman during the normal course of his/her day and through his/her usual daily activities and routine including—but not limited to sports, physical activity, cleaning, gardening, shopping. This includes the full spectrum of workout routines common to men/women including—but not limited to yoga, pilates, walking, running, tennis, golf, hiking, martial arts, dance, biking.

In some examples, the garment 100 can be designed to treat Osteoporosis by increasing bone mass and decrease risk of osteoporotic fractures; designed to treat generalized deconditioning to improve strength, balance and flexibility; designed to increase bone mass; designed to treat functional Kyphosis (functional due to long hours bent over desk, computer, driving, etc.); designed to treat Scoliosis; designed to treat back pain due to stiffness and muscle spasm; designed to treat compression fractures and other painful thoracic spine pathologies; designed to treat anxiety and/or; designed to treat autism.

In some examples weights are arranged over and along either or both sides of the spine. In that case it can be advantageous to have soft, flexible weighs. One soft weight would be a gel impregnated with small pieces of a heavy metal such as lead. A mesh may be entrained (e.g., embedded) in the gel creating a "sewable", soft, weight.

In some examples, the garment 100 can be designed to sport a slim silhouette so that the man and/or woman can wear it throughout the day—including to his/her place of employment or to many social events—without it being noticeable. This allows the wearer to receive the therapeutic benefit for longer periods of time. Also allows for use during supine and inverted exercises as in Pilates or yoga.

In some examples, the garment 100 can be configured to maintain therapeutic modality firmly against wearer's body with minimal to no shift in position during activity. This is to maintain spine in physiologic position.

In some examples, the garment 100 can be fitted to wearer to provide a fitted garment and prevent unwanted movement of the weights 150 and/or inserts 185.

Figure 14A:
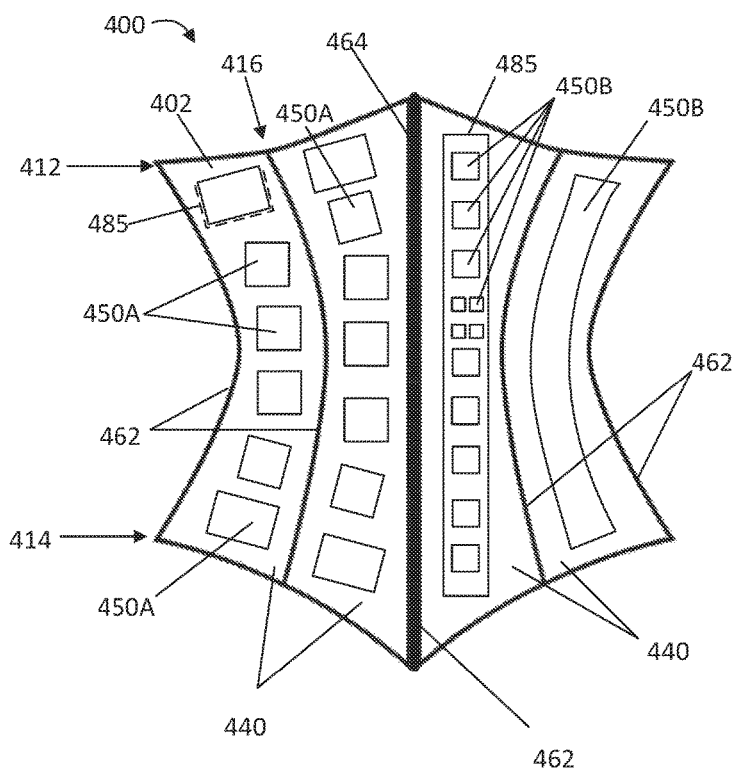
FIGS. 14A and 14B depict front and back views of another garment, in accordance with at least one example.
Figure 14B:
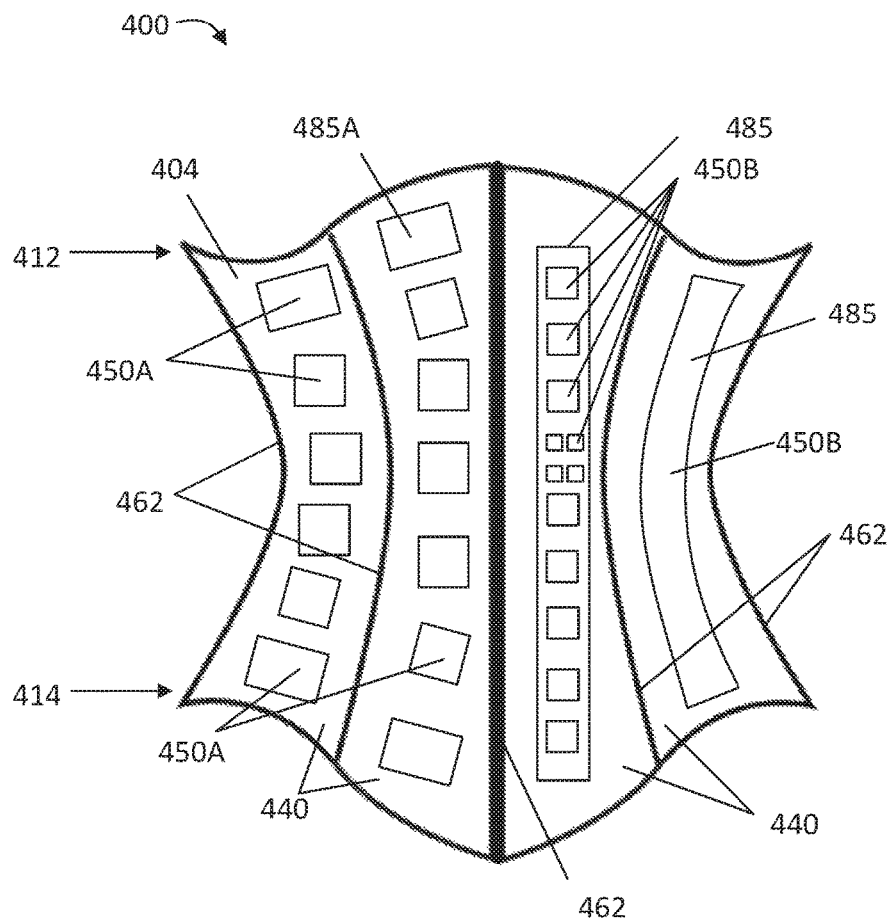
Figure 15A:
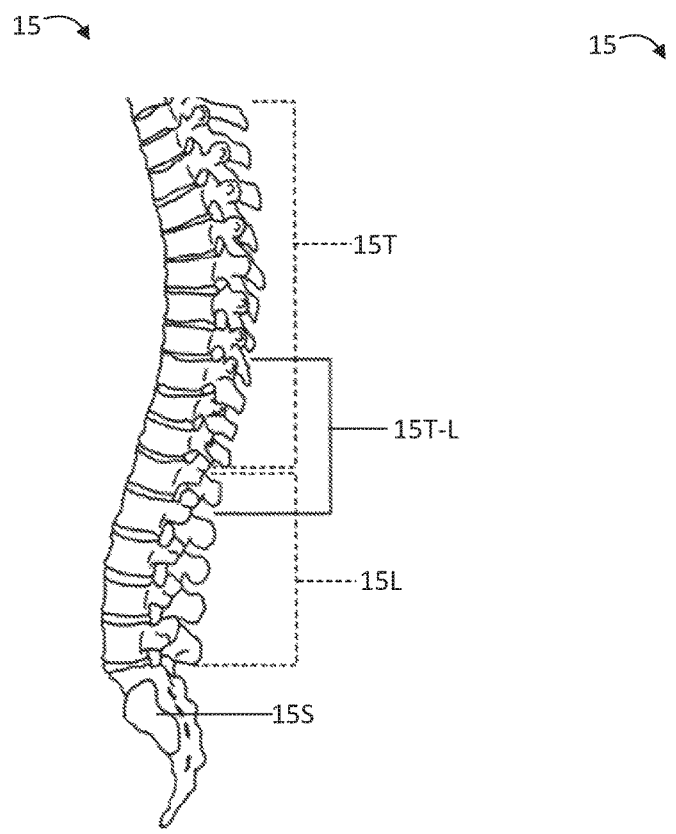
FIGS. 15A and 15B depict posterior and lateral views of a portion of a spine of a human including the thoracic, thoracolumbar, lumbar and sacral spine.
Figure 15B:
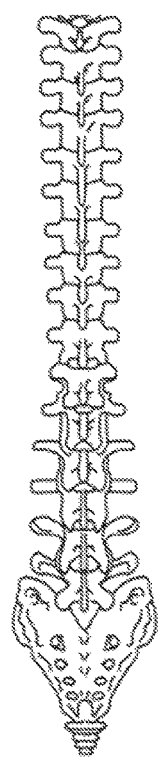

In some examples, the garment 100, and other exemplary garments such as garment 400 of FIGS. 14A and 14B can employ incremental weight placement to help maintain neutral and physiologic spine position. This allows for use by deconditioned wearers, enhanced safety, maintenance of appropriate center of gravity, recruitment of the (smaller) muscles of the postural spine. An example of a human spine is depicted in FIGS. 15A and 15B. Light and immobile weight placement over thoracic 15T, thoracolumbar 15T-L, lumbar 15L and/or sacral 15S spine allows for (self) assisted stretch during targeted exercises resulting in increased flexibility to the user.

Figure 8:
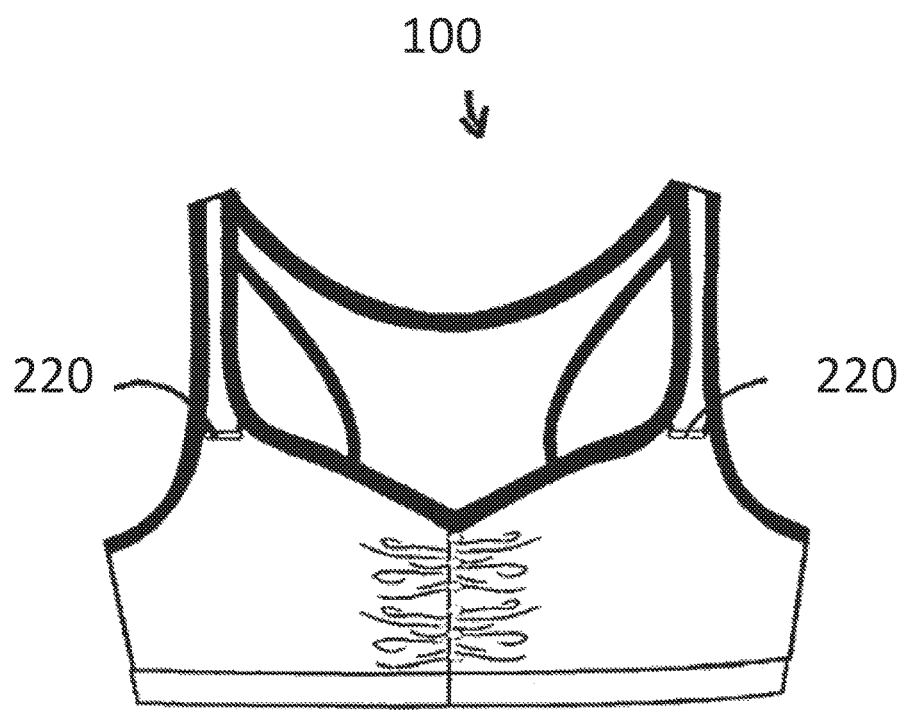
FIG. 8 depicts another garment, in accordance with at least one example.

In some examples, the garment 100 can include adjustable straps 220 as shown in FIG. 8. In some examples, the garment 100 composes at least one compartment 230 positioned under the user's armpit where back section 130 and front section 120 are coupled with each other. In some embodiment, the compartment 230 is coupled with an inner surface of the garment 100, wherein the inner surface of the garment 100 is the closest to the user's skin. In some embodiment, the compartment 230 is coupled with an outer surface of the garment 100, wherein the outer surface of the garment 100 is the farthest from the user's skin. In some examples, the compartment 230 is sewn to, glued to, and/or Velcro with the garment 100. In some examples, the compartment 230 is removably coupled with the garment 100.

Figure 10:
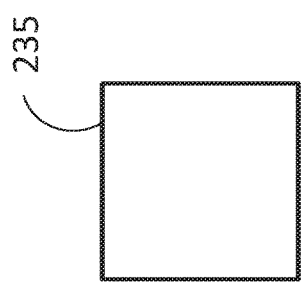
FIG. 10 depicts another insert, in accordance with at least one example.
Figure 11:
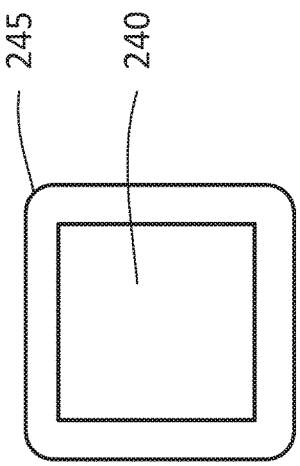
FIG. 11 depicts another insert, in accordance with at least one example.
Figure 9:
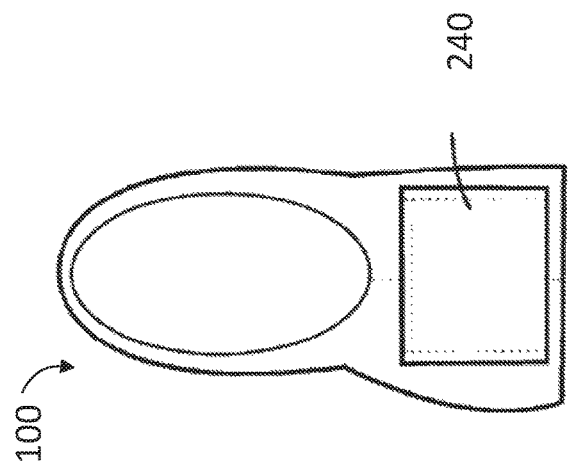
FIG. 9 depicts another garment, in accordance with at least one example.

In some examples, the compartment 230 is configured to accommodate at least one insert 235 as shown in FIG. 10. In some examples, the insert 235 can include metal, polymer, silicone, rubber and/or combination of these and/or other suitable materials. In some examples, the insert 235 can include metal 240 incased in soft material 245 as shown in FIG. 11. In some embodiment, the soft material 245 is silicone, rubber, foam and/or combination of these and/or other suitable materials.

In some examples, the insert 235 can be removably coupled with the compartment 230. In some examples, the insert 235 can be replaceable with another insert (not shown).

In some examples, the garment 100 can include at least one breast compartment positioned under the user's breasts (not shown). In some embodiment, the breast compartment can be coupled with an inner surface of the garment 100, wherein the inner surface of the garment 100 can be the closest to the user's skin. In some embodiment, the compartment 230 can be coupled with an outer surface of the garment 100, wherein the outer surface of the garment 100 can be the farthest from the user's skin. In some examples, the breast compartment can be sewn to, glued to, and/or Velcro with the garment 100. In some examples, the breast compartment can be removably coupled with the garment 100.

In some examples, the breast compartment can be configured to accommodate at least one breast insert (not shown). In some examples, the breast insert can include metal, polymer, silicone, rubber and/or combination of these and/or other suitable materials. In some examples, the breast insert can include metal incased in soft material (not shown). In some examples, the soft material can be silicone, rubber, foam and/or combination of these and/or other suitable materials.

In some examples, the breast insert can be removably coupled with the breast compartment. In some examples, the breast insert can be replaceable with another insert (not shown).

Figure 12:
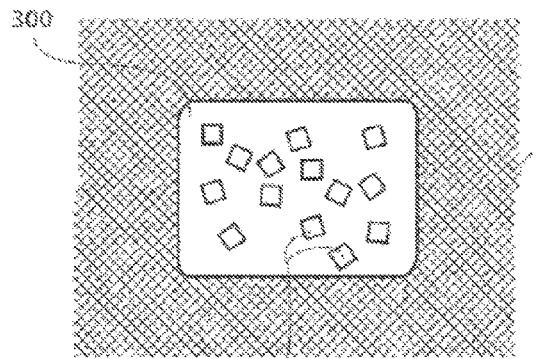
FIGS. 12A, 12B and 12C show, in a schematic form, a sewable, gel-based weight, in accordance with at least one example.
Figure 12:
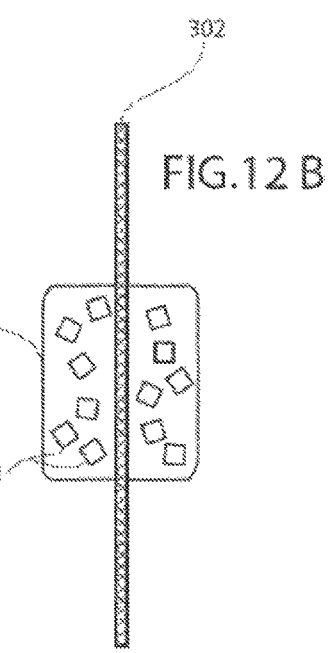
Figure 12:
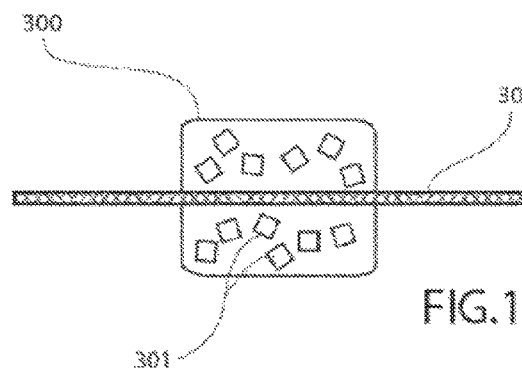

FIGS. 12A, B, and C show, in a schematic form, a sewable, gel-based weight with gel 300, mesh 302 and metal particles 301.

Figure 13:
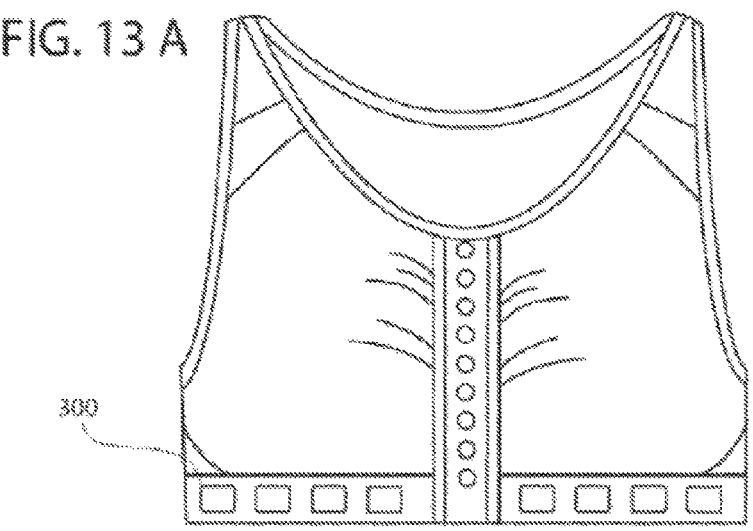
FIGS. 13A and 13B are a front and back view of a bra with gel weighs along the spine and other weights along the lower band in front as counter weight, in accordance with at least one example.
Figure 13:
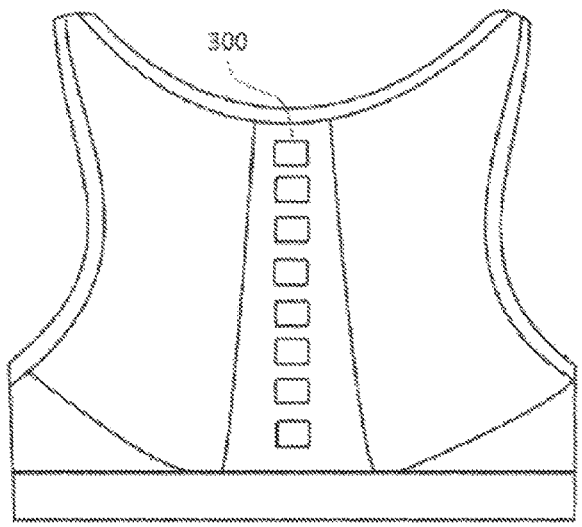

FIGS. 13A and B are a front and back view of a bra with gel weights along the spine and other weights along the lower band in front, as counter weight.

FIGS. 14A and 14B show back and front views of another example garment 400 according to the present disclosure. The garment 400 can include, for example, a waist trainer, a corset, a girdle, a back support, a back brace, or any other suitable garment. Like the garment 100 (e.g., the bra), the garment 400 can include a body 402, 404 and a plurality of weights 450A, 450B. The garment 400 can include any of the features previously described with regard to Garment 100 and FIGS. 1-11, 12A-12B, 13A and 13B. Like numerals may represent like elements.

In some examples, and as shown in FIGS. 14A and 14B, the body 402, 404 can have an elastic portion 440 that can be configured to extend around a torso of a user, and can compress the torso. This compression can be uniform or variable along the body, with certain portions of the garment 400 applying more compression than other portions of the garment 400. In some examples, it may be desirable to provide stronger compression in the region of a particular muscle or vertebrae of the user, depending on the needs of the person. The amount and location of compression can be tailored to a specific person based on a physical assessment, an imaging (e.g., MIII, X-ray or CT scan) assessment, or a surgical assessment of the person. For example what surgery has the person had, is a candidate for, or will have?

The body 402, 404 can extend from an upper end portion 412 (e.g., first end portion) to a lower end portion 414 (e.g., second end portion). The garment 400 can be wrapped around a user and secured at a closure 464 (FIG. 14A). Closure 464 can include hook and loop, hooks and eyes, snaps, buttons, zippers, lacing, or any other suitable closure device. The body 402, 404 can also include one or more compartments 480 (FIG. 14A) including any of the features described for compartments 180 (FIG. 2).

The body 402, 404 and the plurality of weights 450A, 450B can provide targeted training of small muscles along any of: a thoracic spine 15T, a thoracolumbar spine 15 T-L, a lumbar spine 15L, and a sacral spine 15S of the user (Spine 15 in FIGS. 15A and 15B). The plurality of weights 450A, 450B can be distributed and arranged along the body 402, 404. The plurality of weights 450A, 450B show different examples of weights which can be incorporated into inserts 485 similar to the inserts 185 (FIG. 7). In some examples, the plurality of weights 450A, 450B can be movable relative to one another with movement of the vertebrae of the user's spine (15, FIG. 15). The plurality of weights 450A, 450B can be configured to move in a corresponding motion with the vertebrae of the user. The body 402, 404 and the plurality of weights 450A, 450B can be configured to conform to the fleshy part of a user's body and to provide deep touch pressure compression of the plurality of weights 450A, 450B to the torso to target the small postural muscles supporting the desired portion of the spine of a user when worn by the user to engage and train the small postural muscles of the spine.

The plurality of weights 450A, 450B (e.g., inserts 485), can include any of the features previously described with regard to the plurality of weights 150, or any other of the weights or inserts described herein in FIGS. 1-11, 12A-12B, 13A and 13B. In general, the individual weights can be in the range of 4-8 ounces (oz.) each, and the total weight carried in the garment can be in the range of 1.5-5 pounds (lbs.). In a possibly more preferred example, depending on the user, the individual weights can be in the range of 4-6 ounces, and the total weight carried can be in the range of 3-4 lbs.

The garment 400 can be a corset that includes one or more reinforcement members 462 such as boning. The reinforcement members 462 can keep the garment from curling over, especially at the first end portion 412 and the second end portion 414. The reinforcement members 462 can be made of plastic, spring metal, metal coil, or any other suitable material. The reinforcement members 462 may be inserted into a channel 416 (FIG. 14A) between two layers of fabric. In the front view, for example, the corset can cover at least a portion of the area from the collar bone or sternum down to the pelvic area, and in the back view, the corset can cover from the shoulder down to below the buttocks. The corset can include an under bust corset as shown, or the corset can incorporate a bust portion, but can also be any other type of corset. The plurality of weights 450A, 450B may be positioned in between reinforcement members 462 (e.g., positioned laterally in between reinforcement members 462 from side to side of the garment 400), as shown in FIGS. 14A and 14B.

Corsets work by increasing the pressure in the abdomen, thus reducing the amount of weight placed on sensitive spinal structures, such as vertebrae and joints. By reducing the stress on these structures, the spine and the muscles, tendons and ligaments surrounding the spine can heal faster. Corsets can also be used to change the silhouette of a user.

The garment 400 can also incorporate under arm weights, breast inserts, or an elastic portion, as previously described with respect to garment 100. In the case of the elastic portion 440, it can include an elastic band portion (e.g., like at 140, FIGS. 1 and 2) that is in the form of an elastic band of material that applies more compression to the torso than the adjacent material, and can have weights disposed thereon in a manner similar to FIGS. 7 and 13A on elastic portion 140 of FIGS. 1 and 2. The elastic band can be a separate elastic band from the rest of the elastic portion, or could be a portion of the elastic portion folded onto itself to create stronger compression at the folded over region.

The garment 400 can include a spinal brace that is made of lightweight cloth. In the example of a brace, the garment 400 could include reinforcement members (e.g., 462, but can be positioned and sized differently than in the example of a corset). Such reinforcement member 462 can restrict movement and help improve posture. The reinforcement members 462 can be added or removed based on the treatment needs. The reinforcement members can be substantially rigid or flex a maximum between a range of 15 to 45 degrees, or in a possibly more preferred example, flex a maximum between a range of 10 and 30 degrees, and in an even more preferred embodiment flex a maximum between a range of 10 and 20 degrees. For instance, if a person needs a spinal brace to help recover from lumbar spine surgery, the one or more reinforcement members 462 can restrict movement and allow the sensitive surgical area to heal easier, and as more motion is allowable, the reinforcement members 462 could be removed part of the time of a day or removed altogether. In the case of a back brace, the reinforcement members 462 could be aligned with a spine of the user, or muscles along the side of the user, and be more rigid than the example of boning described herein.

An example of a human spine is shown in FIGS. 15A and 15B. Example garments can include garments such as the garments 100, 400 that engage the spine 15 as a whole or can be tailored to engage only portions of the spine 15. In some examples, the garments (e.g., 100, 400) can be configured to position the plurality of weights, or inserts (e.g., 185, 485) at least partially over any of: the thoracic spine 15T posteriorly from T1-T12, the lumbar spine 15T (e.g., L1-L5), the thoracolumbar spine 15T-L and the sacral spine 15S (e.g., S1-S5) and may extend laterally as far as the lateral aspect of the scapula, or extend further around the torso to engage the anterior portion of the user including the obliques and/or the abdominals. The garments 100, 400 can recruit and strengthen the muscles of the user's back and to weight load the user's spine and other core muscles. Muscles affected by garments 100, 400 can include those responsible for posture, for spinal mobility, and muscles of the shoulder girdle. Example muscles include but are not limited to the paraspinal muscles, erector spinae, multifidus, trapezius, rhomboids, serratus anterior, levator scapulae, the rectus abdominis, the transverse abdominis, the external and internal obliques.

The erector spinae can include the iliocostalis, the longissimus, or the spinalis. Muscles can also include the deep intrinsic muscles located underneath the erector spinae. They are a group of short muscles, associated with the transverse and spinous processes of the vertebral column. There are three major muscles in this group, the semispinalis, the multifudus and the rotatores. Multifudus muscles are very short muscles running from the transverse processes (on the sides) of the vertebra, up to the spinous process (the middle of the back) of the next vertebra upwards. The main function of the multifudus muscles is back stability. They do not produce a large range of movement, but work to produce small fine-tuning postural movements, all day long or as long as the user wears the garment.

Weight loading of the user's spine helps to preserve bone mass density and to slow the age related loss of bone mass. In addition, this positioning of the weight serves to potentiate postural and upper body exercises by increasing the workload of the muscles involved. The weights can also serve to engage postural muscles during normal daily activity. Stronger back muscles reduce the incidence of vertebral fractures.

Throughout the course of normal daily activity, the human torso and spine moves three dimensionally in the coronal, the sagittal and the transverse planes. Circumferential placement of weights, as provided in the garment 400, as well as the garment 100, ensures that these core stability muscles can be engaged, challenged and exercised through all three natural planes of motion (e.g., the sagittal, transverse and coronal), throughout the range of motion during the course of normal daily activity. The sagittal plane passes through the body from front to back and divides it into left and right sides. The coronal plane divides the body into front and back. The transverse plane divides the body into top and bottom.

The weights 450A, 450B, rather than extending along a longitudinal direction as shown, could also be shaped and arranged to extend circumferentially around the torso in a lateral direction around the garment.

In some examples, the garments (e.g., 100, 400) can be configured to strengthen back muscles whereby it has been found that strengthening of back muscles (markedly) decreases incidence/risk of vertebral fracture. In some examples, the garments 100, 400 can be configured to increase level of exertion, even if at a low level, whereby it has been found that even a low level of physical activity helps cut mortality risk. In some examples, the example garments can be configured to increase the number of calories burned each hour regardless of physical activity.

In some examples, the garments (e.g., 100, 400) can be configured to provide the benefits of strength training. Studies have shown that strength training benefits women and men of all ages and all levels of fitness. Experts agree that aerobic activities should be supplemented with strength training. Strength training will: build strength; maintain bone density; improve balance, coordination, and mobility; reduce your risk of falling; maintain independence in performing activities of daily life for the elderly and the debilitated.

There are numerous benefits to strength training regularly, particularly as you grow older. It can be very powerful in reducing the signs and symptoms of numerous diseases and chronic conditions, among them: arthritis; diabetes; osteoporosis; obesity; back pain; depression; insomnia.

In some examples, the garments (e.g., 100, 400) can be configured to provide convenience of workout allowing wearer to incorporate exercises in the normal routine of the day because it has been shown an exercise program incorporating strength and balance training into daily activities helped seniors maintain functional capacity better than traditional training.

In some examples, the garments (e.g., 100, 400) can be configured to help align posture to sagittal balance because it has been shown that correctly aligned posture helps to reduce back and joint pain.

In some examples, the garments (e.g., 100, 400) can be specifically designed with low level of weight to decrease stress to joints and spine.

As shown, the garment can be configured to be discreet, convenient, and comfortable.

In some examples, the presently disclosed garment or portions of garment are configured to fit in a manner providing deep touch pressure—functionally similar to that of Temple Grandin's hug box, swaddling of babies, or weighted vests and blankets used in autism to reduce anxiety and nervousness.

While several illustrative examples of the invention have been shown and described, numerous variations and alternative examples will occur to those skilled in the art. Such variations and alternative examples are contemplated, and can be made without departing from the scope of the invention as defined in the appended claims.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The term "plurality" includes two or more referents unless the content clearly dictates otherwise. Unless defined otherwise, all technical and scientific terms used herein have the same meaning as commonly understood by one of ordinary skill in the art to which the disclosure pertains.

The foregoing detailed description of exemplary and preferred examples is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary examples which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claimed element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ".

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

VARIOUS NOTES AND EXAMPLES

To better illustrate the devices and methods disclosed herein, a non-limiting list of embodiments is provided herein.

Example 1 is a garment or portion of a garment to provide targeted training of small muscles along a thoracic spine of a user, the garment or portion of a garment comprising: a body configured to extend around a torso of a user, the body extending from an upper end portion to a lower end portion; a plurality of weights distributed and arranged along the body, wherein the body and the plurality of weights are configured to conform to the fleshy part of a user's body and to provide deep touch pressure compression of the plurality of weights to the torso to target the small postural muscles supporting the thoracic spine of a user when worn by the user to engage and train the small postural muscles of the thoracic spine, wherein the plurality of weights are movable relative to one another with movement of the vertebrae of the user's spine, and the weights are configured to move in a corresponding motion with the vertebrae of the user.

In Example 2, the subject matter of Example 1 includes, wherein the plurality of weights provide deep touch pressure compression of the weights to the torso to target the small postural muscles supporting the lumbar spine of a user when worn by the user.

In Example 3, the subject matter of Examples 1-2 includes, wherein the plurality of weights provide deep touch pressure compression of the weights to the torso to target the small postural muscles supporting the sacral spine of a user when worn by the user.

In Example 4, the subject matter of Examples 1-3 includes, wherein the plurality of weights provide deep touch pressure compression of the weights to the torso to target the small postural muscles supporting the lumbar spine and the sacral spine when worn by the user.

In Example 5, the subject matter of Examples 1-4 includes, wherein the garment or portion of a garment comprises a waist trainer.

In Example 6, the subject matter of Examples 1-5 includes, wherein the garment or portion of a garment comprises a back brace.

In Example 7, the subject matter of Examples 1-6 includes, wherein the body comprises boning.

In Example 8, the subject matter of Examples 1-7 includes, wherein the body comprises a longitudinal structure extending from the upper end portion to the lower end portion to prevent curling of the upper end portion and the lower end portion.

In Example 9, the subject matter of Examples 1-8 includes, wherein the plurality of weights are located such that, when worn, the weights apply deep touch pressure compression to muscles of the user to increase the work load these muscles must overcome to function.

In Example 10, the subject matter of Example 9 includes, wherein the muscles that the weights apply deep touch pressure compression to comprise at least one of: an erector spinae, a multifidus, a semispinalis, a rotatores, an external oblique, an internal oblique, a transverse abdominis, a rectus abdominis.

Example 11 is a garment or portion of a garment to provide targeted training of small muscles along a thoracolumbar spine of a user, the garment or portion of a garment comprising: a body configured to extend around a waist of a user, the body extending from an upper end portion to a lower end portion; a plurality of weights distributed and arranged along the body, wherein the body and the plurality of weights are configured to conform to the fleshy part of a user's body and to provide deep touch pressure compression of the plurality of weights to the waist to target the small postural muscles supporting the thoracolumbar spine of a user when worn by the user to engage and train the small postural muscles of the thoracolumbar spine, wherein the plurality of weights are movable relative to one another with movement of the vertebrae of the user's spine, and the weights are configured to move in a corresponding motion with the vertebrae of the user.

In Example 12, the subject matter of Examples 1-11 includes, wherein the plurality of weights provide deep touch pressure compression of the weights to the waist to target the small postural muscles supporting the lumbar spine of a user when worn by the user.

In Example 13, the subject matter of Examples 1-12 includes, wherein the plurality of weights provide deep touch pressure compression of the weights to the torso to target the small postural muscles supporting the sacral spine of a user when worn by the user.

In Example 14, the subject matter of Examples 1-13 includes, wherein the garment or portion of the garment comprises a waist trainer.

In Example 15, the subject matter of Examples 1-14 includes, wherein the body comprises boning.

In Example 16, the subject matter of Examples 1-15 includes, wherein the body comprises a longitudinal structure extending from the upper end portion to the lower end portion to prevent curling of the upper end portion and the lower end portion.

In Example 17, the subject matter of Examples 1-16 includes, wherein the body comprises a channel, and wherein boning is disposed in the channel.

In Example 18, the subject matter of Examples 1-17 includes, wherein the plurality of weights are located such that, when worn, the weights apply deep touch pressure compression to muscles of the user to increase the work load these muscles must overcome to function.

In Example 19, the subject matter of Example 18 includes, wherein the muscles that the weights apply deep touch pressure compression to comprise at least one of: an erector spinae, a multifidus, a semispinalis, a rotatores, an external oblique, an internal oblique, a transverse abdominis, a rectus abdominis.

Example 20 is a garment or portion of a garment to provide targeted training of small muscles along a lumbar spine of a user, the garment or portion of a garment comprising: a body configured to extend around a waist of a user, the body extending from an upper end portion to a lower end portion; a plurality of weights distributed and arranged along the body, wherein the body and the plurality of weights are configured to conform to the fleshy part of a user's body and to provide deep touch pressure compression of the plurality of weights to the waist to target the small postural muscles supporting the lumbar spine of a user when worn by the user to engage and train the small postural muscles of the lumbar spine, wherein the plurality of weights are movable relative to one another with movement of the vertebrae of the user's spine, and the weights are configured to move in a corresponding motion with the vertebrae of the user.

Example 22 is an apparatus comprising means to implement of any of Examples 1-20.

Example 23 is a system to implement of any of Examples 1-20.

Example 24 is a method to implement of any of Examples 1-20.

What is claimed is:

1. A garment or portion of a garment to provide targeted training of small muscles along a thoracic spine of a user, the garment or portion of a garment comprising:
    a body configured to extend around a torso of a user, the body extending from an upper end portion to a lower end portion;
    a plurality of weights distributed and arranged along the body, wherein the body and the plurality of weights are configured to conform to the fleshy part of a user's body and to provide deep touch pressure compression of the plurality of weights to the torso to target the small postural muscles supporting the thoracic spine of a user when worn by the user to engage and train the small postural muscles of the thoracic spine, wherein the plurality of weights are movable relative to one another with movement of the vertebrae of the user's spine, and the weights are configured to move in a corresponding motion with the vertebrae of the user.

2. The garment or portion of the garment of claim 1, wherein the plurality of weights provide deep touch pressure compression of the weights to the torso to target the small postural muscles supporting the lumbar spine of a user when worn by the user.

3. The garment or portion of the garment of claim 1, wherein the plurality of weights provide deep touch pressure compression of the weights to the torso to target the small postural muscles supporting the sacral spine of a user when worn by the user.

4. The garment or portion of the garment of claim 1, wherein the plurality of weights provide deep touch pressure compression of the weights to the torso to target the small postural muscles supporting the lumbar spine and the sacral spine when worn by the user.

5. The garment or portion of the garment of claim 1, wherein the garment or portion of a garment comprises a waist trainer.

6. The garment or portion of a garment of claim 1, wherein the garment or portion of a garment comprises a back brace.

7. The garment or portion of the garment of claim 1, wherein the body comprises boning.

8. The garment or portion of the garment of claim 1, wherein the body comprises a longitudinal structure extending from the upper end portion to the lower end portion to prevent curling of the upper end portion and the lower end portion.

9. The garment or portion of the garment of claim 1, wherein the plurality of weights are located such that, when worn, the weights apply deep touch pressure compression to muscles of the user to increase the work load these muscles must overcome to function.

10. The garment or portion of the garment of claim 9, wherein the muscles that the weights apply deep touch pressure compression to comprise at least one of: an erector spinae, a multifidus, a semispinalis, a rotatores, an external oblique, an internal oblique, a transverse abdominis, a rectus abdominis.

11. A garment or portion of a garment to provide targeted training of small muscles along a thoracolumbar spine of a user, the garment or portion of a garment comprising:
    a body configured to extend around a waist of a user, the body extending from an upper end portion to a lower end portion;
    a plurality of weights distributed and arranged along the body, wherein the body and the plurality of weights are configured to conform to the fleshy part of a user's body and to provide deep touch pressure compression of the plurality of weights to the waist to target the small postural muscles supporting the thoracolumbar spine of a user when worn by the user to engage and train the small postural muscles of the thoracolumbar spine, wherein the plurality of weights are movable relative to one another with movement of the vertebrae of the user's spine, and the weights are configured to move in a corresponding motion with the vertebrae of the user.

12. The garment or portion of the garment of claim 11, wherein the plurality of weights provide deep touch pressure compression of the weights to the waist to target the small postural muscles supporting the lumbar spine of a user when worn by the user.

13. The garment or portion of the garment of claim 11, wherein the plurality of weights provide deep touch pressure compression of the weights to the torso to target the small postural muscles supporting the sacral spine of a user when worn by the user.

14. The garment or portion of the garment of claim 11, wherein the garment or portion of the garment comprises a waist trainer.

15. The garment or portion of the garment of claim 11, wherein the body comprises boning.

16. The garment or portion of the garment of claim 11, wherein the body comprises a longitudinal structure extending from the upper end portion to the lower end portion to prevent curling of the upper end portion and the lower end portion.

17. The garment or portion of the garment of claim 11, wherein the body comprises a channel, and wherein boning is disposed in the channel.

18. The garment or portion of the garment of claim 11, wherein the plurality of weights are located such that, when worn, the weights apply deep touch pressure compression to muscles of the user to increase the work load these muscles must overcome to function.

19. The garment or portion of the garment of claim 18, wherein the muscles that the weights apply deep touch pressure compression to comprise at least one of: an erector spinae, a multifidus, a semispinalis, a rotatores, an external oblique, an internal oblique, a transverse abdominis, a rectus abdominis.

20. A garment or portion of a garment to provide targeted training of small muscles along a lumbar spine of a user, the garment or portion of a garment comprising:
- a body configured to extend around a waist of a user, the body extending from an upper end portion to a lower end portion;
- a plurality of weights distributed and arranged along the body, wherein the body and the plurality of weights are configured to conform to the fleshy part of a user's body and to provide deep touch pressure compression of the plurality of weights to the waist to target the small postural muscles supporting the lumbar spine of a user when worn by the user to engage and train the small postural muscles of the lumbar spine, wherein the plurality of weights are movable relative to one another with movement of the vertebrae of the user's spine, and the weights are configured to move in a corresponding motion with the vertebrae of the user.

* * * * *